United States Patent
Ohta et al.

(10) Patent No.: US 7,985,955 B2
(45) Date of Patent: *Jul. 26, 2011

(54) RADIATION DETECTING CASSETTE AND RADIATION IMAGE CAPTURING SYSTEM

(75) Inventors: Yasunori Ohta, Yokohama (JP); Eiichi Kito, Minami-ashigara (JP); Tsuyoshi Tanabe, Odawara (JP); Takuya Yoshimi, Yokohama (JP)

(73) Assignee: Fujifilm Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/801,881

(22) Filed: Jun. 30, 2010

(65) Prior Publication Data
US 2010/0271215 A1 Oct. 28, 2010

Related U.S. Application Data

(63) Continuation of application No. 12/222,848, filed on Aug. 18, 2008, now Pat. No. 7,772,560.

(30) Foreign Application Priority Data

| Aug. 16, 2007 | (JP) | 2007-212244 |
| Jan. 31, 2008 | (JP) | 2008-020106 |
| May 30, 2008 | (JP) | 2008-143454 |

(51) Int. Cl.
*G01T 1/00* (2006.01)
(52) U.S. Cl. ........... 250/370.09; 340/687; 715/709
(58) Field of Classification Search .............. 715/709; 340/687; 250/370.09
See application file for complete search history.

(56) References Cited

U.S. PATENT DOCUMENTS

| 7,126,129 B2 * | 10/2006 | Yamamoto | 250/370.09 |
| 2006/0215892 A1 | 9/2006 | Ohara | |
| 2006/0242094 A1 | 10/2006 | Tamakoshi | |

FOREIGN PATENT DOCUMENTS

| JP | 07-140255 | 6/1995 |
| JP | 2005-007086 | 1/2005 |
| JP | 2005-208269 | 8/2005 |
| WO | WO 2005058416 A1 * | 6/2005 |

* cited by examiner

*Primary Examiner* — Constantine Hannaher
(74) *Attorney, Agent, or Firm* — Jean C. Edwards, Esq.; Edwards Neils PLLC

(57) ABSTRACT

A radiation detecting cassette and a radiation image capturing system are provided. A radiation detecting cassette has a radiation detector for detecting a radiation having passed through a patient and converting the detected radiation into radiation image data, a transceiver for transmitting the radiation image data by way of wireless communications, a cassette controller for controlling the radiation detector and the transceiver, a power supply for energizing the radiation detector and the transceiver, and a remaining power supply power level detector for detecting a remaining power level RC [%] of the power supply. The cassette controller includes a data transmission and reception controller. The cassette controller stops transmitting the radiation image data by way of wireless communications and prioritizes the capturing of a radiation image when the detected remaining power level of the power supply is smaller than a predetermined threshold.

1 Claim, 11 Drawing Sheets

RADIATION DETECTING CASSETTE AND RADIATION IMAGE CAPTURING SYSTEM

CROSS-REFERENCE TO RELATED APPLICATIONS

The present application is a Continuation Application of U.S. patent application Ser. No. 12/222,848, filed on Aug. 18, 2008 now U.S. Pat. No. 7,772,560, which claims priority from Japanese Patent Application No. 2007-212244, filed on Aug. 16, 2007, Japanese Patent Application No. 2008-020106, filed on Jan. 31, 2008, and Japanese Patent Application No. 2008-143454, filed on May 30, 2008, the contents of all of which are herein incorporated by reference in their entirety.

BACKGROUND OF THE INVENTION

1. Field of the Invention

The present invention relates to a radiation detecting cassette having therein a radiation conversion panel for detecting a radiation that has passed through a subject and converting the detected radiation into radiation image data, and a radiation image capturing system incorporating such a radiation detecting cassette, and more particularly the present invention relates to a radiation detecting cassette for transmitting radiation image data to an external device by way of wireless communications, and a radiation image capturing system incorporating such a radiation detecting cassette.

2. Description of the Related Art

In the medical field, there have widely been used radiation image capturing apparatus which apply a radiation to a subject and guide the radiation that has passed through the subject to a radiation conversion panel, which captures a radiation image from the radiation. Known forms of the radiation conversion panel include a conventional radiation film for recording a radiation image by way of exposure, and a stimulable phosphor panel for storing a radiation energy representing a radiation image in a phosphor and reproducing the radiation image as stimulated light by applying stimulating light to the phosphor. In such a radiation conversion panel, the radiation film with the recorded radiation image is supplied to a developing device to develop the radiation film, or the stimulable phosphor panel is supplied to a reading device to read the radiation image, to obtain the radiation image as a visible image.

In the medical examination room or the like, it is necessary to read out and display a recorded radiation image immediately from a radiation conversion panel after the radiation image is captured for the purpose of quickly and appropriately treating the patient. As a radiation conversion panel which meets such a requirement, there has been developed a radiation detector having a solid-state detector for converting a radiation directly into an electric signal or converting a radiation into visible light with a scintillator and then converting the visible light into an electric signal to read out a detected radiation image. The radiation conversion panel is separate from a console as a controller and a radiation source because the radiation conversion panel is used to capture radiation images of various areas of patients (see Japanese Patent No. 3494683, Japanese Laid-Open Patent Publication No. 2005-007086, and Japanese Laid-Open Patent Publication No. 2005-208269).

According to the technology disclosed in Japanese Patent No. 3494683, a radiation detecting cassette (hereinafter also referred to as "cassette") having therein a radiation conversion panel transmits a radiation image signal as a wireless signal to an external signal processor (Paragraph [0043], FIG. 5 of Japanese Patent No. 3494683). According to the technology disclosed in Japanese Laid-Open Patent Publication No. 2005-007086, the remaining power level of a battery is detected, and the number of radiation images that can be captured is calculated (Paragraph [0033] of Japanese Laid-Open Patent Publication No. 2005-007086). According to the technology disclosed in Japanese Laid-Open Patent Publication No. 2005-208269, the remaining power level of a battery is detected, and the application of X-rays is canceled if the detected remaining power level is smaller than a predetermined value (Paragraphs [0017]-[0022] of Japanese Laid-Open Patent Publication No. 2005-208269).

According to Japanese Patent No. 3494683, a radiation detector (a solid-state detector, a scanning pulse generator, and a transfer register) and a transmission processing circuit are energized by a single power supply (Paragraphs [0033] and [0041] of Japanese Patent No. 3494683). Since the electric power from the power supply is used both for radiation detection and for wireless data transmission, the electric power from the power supply is consumed faster than if it is used only for radiation detection. As a result, the amount of electric power from the power supply which is necessary to capture a required number of radiation images may possibly run short quickly.

According to Japanese Laid-Open Patent Publication No. 2005-007086 and Japanese Laid-Open Patent Publication No. 2005-208269, though the remaining power level of the battery is detected and X-ray images are captured depending on the detected remaining power level of the battery, nothing is shown about the acquisition of radiation image data through the effective use of a low remaining battery power level.

SUMMARY OF THE INVENTION

It is an object of the present invention to provide a radiation detecting cassette which is capable of acquiring radiation image data even when the remaining power level of a power supply is low, through the effective use of the low remaining power supply power level, and a radiation image capturing system incorporating such a radiation detecting cassette.

A radiation detecting cassette according to the present invention comprises a radiation conversion panel for detecting a radiation having passed through a subject and converting the detected radiation into radiation image data, a wireless communication unit for transmitting the radiation image data by way of wireless communications, a control unit for controlling the radiation conversion panel and the wireless communication unit, a power supply for energizing the radiation conversion panel and the wireless communication unit, and a remaining power level detecting unit for detecting a remaining power level of the power supply, wherein the control unit stops transmitting the radiation image data by way of wireless communications and prioritizes capturing of a radiation image with the radiation conversion panel when the detected remaining power level of the power supply is smaller than a predetermined threshold.

According to the present invention, when the remaining power level of the power supply is smaller than the predetermined threshold, the transmission of the radiation image data by way of wireless communications is stopped, and the capturing of a radiation image with the radiation conversion panel is prioritized. Therefore, when the remaining power level of the power supply is reduced, the electric power of the power supply is supplied preferentially for capturing a radiation image, thereby acquiring radiation image data by effectively using the reduced remaining power level of the power supply.

The predetermined threshold should preferably be variable. The amount of electric power required to capture a radiation image and transmit radiation image data by way of wireless communications changes depending on the number of radiation images to be captured or the like. Since the predetermined threshold is variable, it is possible to set the threshold to a value in view of the required amount of electric power.

The radiation detecting cassette should preferably further comprise a nonvolatile memory for storing the radiation image data, and the control unit should preferably store the radiation image data in the nonvolatile memory while stopping transmitting the radiation image data by way of wireless communications. Consequently, even when the power supply of the radiation detecting cassette is turned off, the radiation image data remain stored in the nonvolatile memory, and the time to transmit the radiation image data to an external device can be determined as desired. The radiation detecting cassette can thus be used conveniently.

The radiation detecting cassette should preferably further comprise a volatile memory for temporarily storing the radiation image data, and the control unit should preferably temporarily store the radiation image data in the volatile memory before transmitting the radiation image data by way of wireless communications.

The radiation detecting cassette should preferably further comprise a wired communication unit for transmitting the radiation image data by way of wired communications, and the control unit should preferably control the wired communication unit to transmit the radiation image data to an external device when the remaining power level of the power supply is smaller than the predetermined threshold and greater than a second threshold which is lower than the predetermined threshold. Since wired communications generally consume less electric power than wireless communications, even if the remaining power level of the power supply is not high enough to transmit radiation image data by way of wireless communications, the radiation image data can be transmitted by way of wired communications. Therefore, radiation image data can be transmitted to an external device earlier than if the transmission of the radiation image data is canceled at all times when the wireless transmission is impossible. Consequently, the radiation detecting cassette can be used conveniently.

The radiation detecting cassette should preferably further comprise a remaining power level display unit for displaying the remaining power level of the power supply, and the remaining power level display unit should preferably display that the remaining power level of the power supply is nil when the remaining power level of the power supply drops to a provisional empty value which is indicative of a power level capable of acquiring radiation image data of at least one radiation image.

Therefore, at the time the remaining power level display unit displays that the remaining power level of the power supply is nil, the operator can be prompted to stop acquiring radiation image data. As a result, the remaining electric power of the power supply can be kept at a level at which radiation image data of at least one radiation image can be acquired. Therefore, the image capturing system can easily meet demands for the acquisition of radiation image data in emergency. Inasmuch as the operator is notified of a reduction in the remaining power level of the power supply, the operator is prompted to recharge the power supply, which thus minimizes its undue deterioration.

The control unit may inhibit the power supply from supplying electric power to the radiation conversion panel when the remaining power level of the power supply drops to the provisional empty value, and may permit the power supply to supply electric power to the radiation conversion panel when a power supply permission instruction is given from an external device. Accordingly, the remaining power of the power supply is reliably kept at a level at which radiation image data of at least one radiation image can be acquired, and the image capturing system can easily meet demands for the acquisition of radiation image data in emergency.

A radiation image capturing system according to the present invention comprises the above radiation detecting cassette and a console for performing wireless communications with the radiation detecting cassette and controlling the radiation detecting cassette. The radiation detecting cassette indicates the remaining power level of the power supply detected by the remaining power level detecting unit to the console. The console instructs the radiation detecting cassette to stop transmitting the radiation image data by way of wireless communications and prioritizes capturing of a radiation image with the radiation conversion panel when the detected remaining power level of the power supply is smaller than the predetermined threshold. The control unit of the radiation detecting cassette stops transmitting the radiation image data by way of wireless communications and prioritizes capturing of the radiation image when instructed by the console.

With the above arrangement, the console, rather than the radiation detecting cassette, stops transmitting the radiation image data by way of wireless communications. Therefore, the burden on the processing sequence of the radiation detecting cassette is reduced, making it possible to simplify the circuit arrangement of the radiation detecting cassette. As the radiation detecting cassette often needs to change its position depending on the area of the subject to be imaged, the radiation detecting cassette is more required to be reduced in weight and increased in durability than the console. The simpler circuit arrangement of the radiation detecting cassette leads to an increase in the overall performance of the radiation image capturing system.

The console may include a remaining power level display unit for displaying the remaining power level of the power supply, and the remaining power level display unit may display that the remaining power level of the power supply is nil when the remaining power level of the power supply drops to a provisional empty value which is indicative of a power level capable of acquiring radiation image data of at least one radiation image. In addition to the advantages provided if the remaining power level display unit is included in the radiation detecting cassette, the radiation image capturing system also has advantages in that the radiation detecting cassette may be reduced in size and weight as the remaining power level display unit does not need to be included in the radiation detecting cassette.

When the remaining power level of the power supply drops to the provisional empty value, the console may transmit a power supply inhibition instruction to the control unit for inhibiting the power supply from supplying electric power to the radiation conversion panel, and the control unit may inhibit the power supply from supplying electric power to the radiation conversion panel in response to the power supply inhibition instruction, and when the console is instructed from an external device to supply electric power from the power supply to the radiation conversion panel, the console may transmit a power supply permission instruction to the control unit for supplying electric power from the power supply to the radiation conversion panel, and the control unit may permit the power supply to supply electric power to the radiation conversion panel in response to the power supply permission instruction. In this case, the radiation detecting cassette may also be reduced in size and weight because the console takes over control from the radiation detecting cassette.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

A. 1st Embodiment

Figure 1:
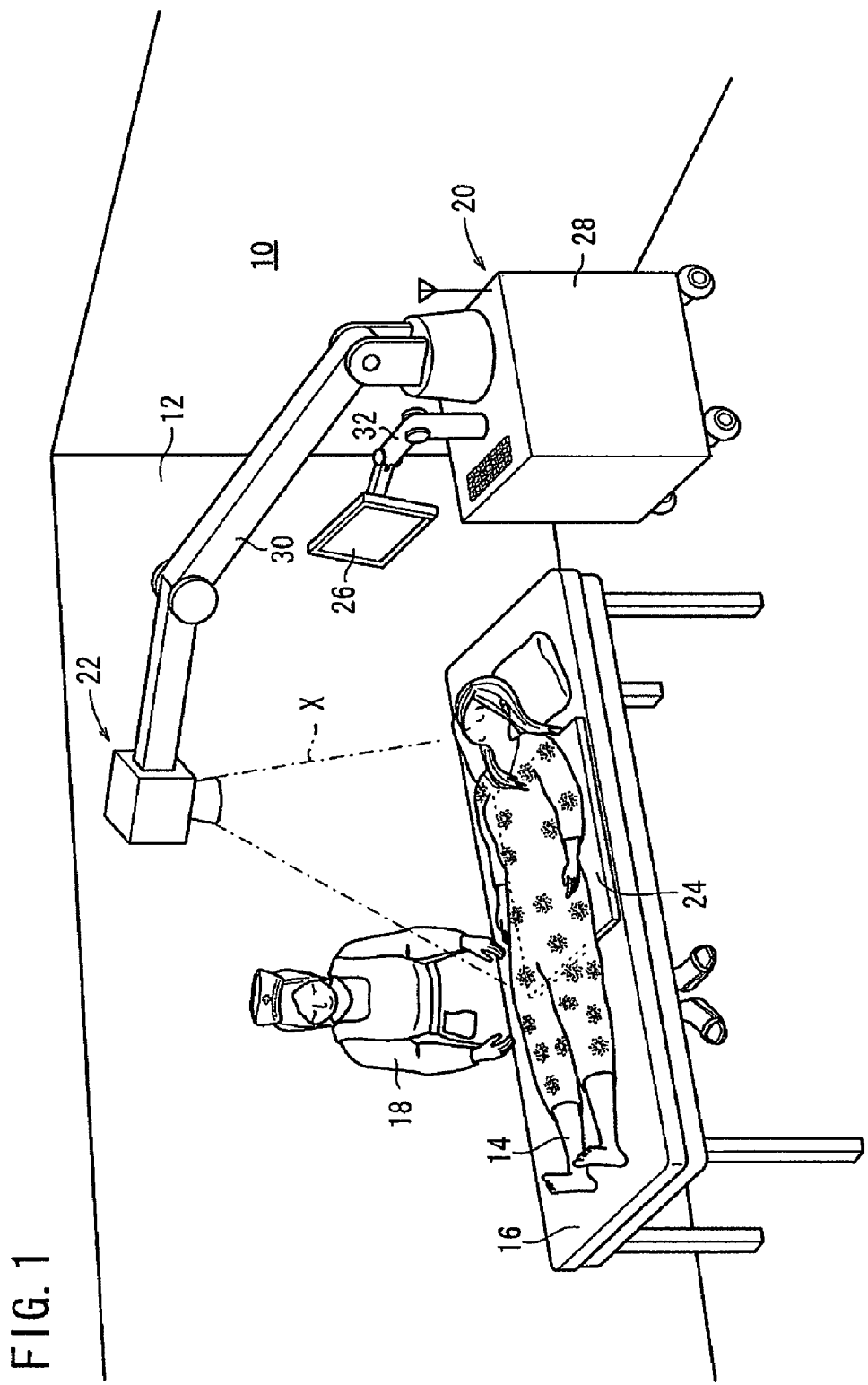
FIG. 1 is a perspective view inside a medical examination room incorporating a radiation image capturing system according to a first embodiment of the present invention.

1. Configuration of Radiation Image Capturing System 10:
(1) Overall Setup:

FIG. 1 shows in perspective a medical examination room 12 incorporating a radiation image capturing system 10 (hereinafter also referred to as "image capturing system 10") according to a first embodiment of the present invention. As shown in FIG. 1, the medical examination room 12 has, in addition to the image capturing system 10, an examination table 16 for a patient 14 to lie thereon.

In the medical examination room 12, the image capturing system 10 includes a radiation image capturing apparatus 20 (hereinafter referred to as "image capturing apparatus 20") for applying a radiation X to the patient 14 and displaying a radiation image of the patient 14, and a radiation detecting cassette 24 (hereinafter referred to as "cassette 24") having therein a radiation detector, to be described later, for detecting the radiation X that has passed through the patient 14.

The image capturing apparatus 20 comprises a radiation irradiating device 22 (hereinafter also referred to as "irradiating device 22") for irradiating the patient 14 with a radiation X at a dose according to radiation image capturing conditions, a display device 26 for receiving radiation image data based on the radiation X from the cassette 24 through a console 28 and displaying a radiation image based on the radiation image data, and a console 28 for controlling the irradiating device 22, the cassette 24, and the display device 26. Signals are transmitted and received between the cassette 24 and the console 28 by way of wireless communications. The cassette 24 and the console 28 may be connected to each other by a cable 49 (see FIG. 2) for transmitting and receiving signals therebetween by way of wired communications.

The irradiating device 22 is coupled to a universal arm 30 so as to be movable to a desired position for capturing a desired area of the patient 14 and also to be retractable to a position out of the way while the doctor 18 or the radiological technician is examining the patient 14. Similarly, the display device 26 is coupled to a universal arm 32 so as to be movable to a position where the doctor 18 can easily confirm a captured radiation image displayed on the display device 26.

Figure 2:
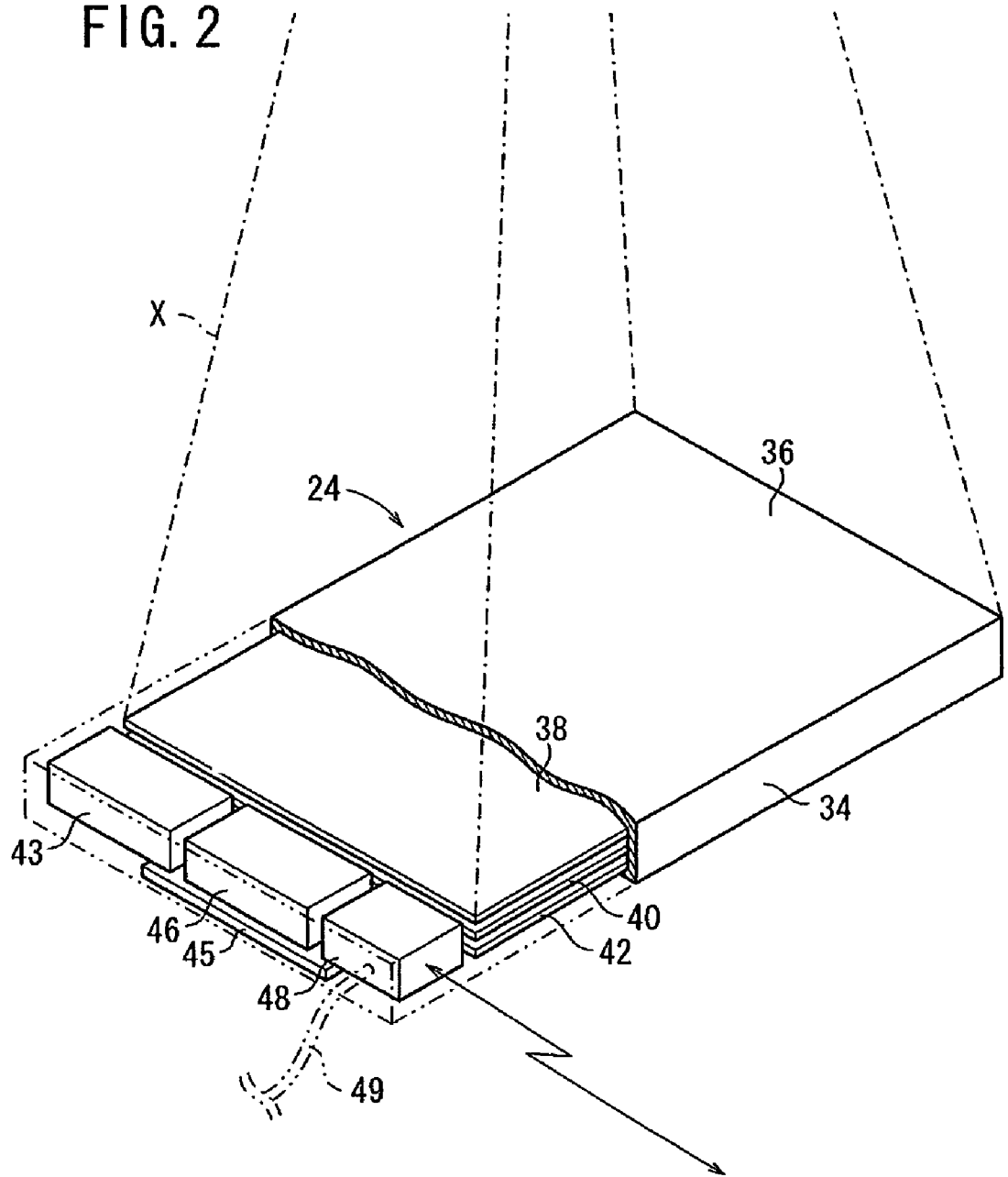
FIG. 2 is a perspective view, partly cut away, showing internal structural details of a radiation detecting cassette used in the radiation image capturing system according to the first embodiment of the present invention.

(2) Radiation Detecting Cassette 24:

FIG. 2 shows internal structural details of the radiation detecting cassette 24. As shown in FIG. 2, the cassette 24 has a casing 34 made of a material permeable to the radiation X. The casing 34 houses therein a grid 38 for removing scattered rays of the radiation X from the patient 14, a radiation detector (radiation conversion panel) 40 for detecting the radiation X that has passed through the patient 14, and a lead plate 42 for absorbing back scattered rays from the radiation X. The grid 38, the radiation detector 40 and the lead plate 42 are successively arranged in that order from a surface 36 of the casing 34 which is irradiated with the radiation X. The irradiated surface 36 of the casing 34 may be constructed as the grid 38.

The casing 34 also houses therein a power supply 43 of the radiation detecting cassette 24, a cassette controller 46 for energizing the radiation detector 40 with electric power supplied from the power supply 43, and a transceiver 48 for transmitting and receiving radiation image data including the information of the radiation X detected by the radiation detector 40, to and from the console 28. The cable 49 for wired communications may be connected to the transceiver 48 for performing wired communications with the console 28. A touch panel 45 for making various settings and displaying messages is mounted on the surface of the casing 34 remote from the irradiated surface 36. A lead plate or the like should preferably be placed over the side surfaces of the cassette controller 46 and the transceiver 48 under the irradiated surface 36 of the casing 34 to protect the cassette controller 46 and the transceiver 48 against damage which would otherwise be caused if irradiated with the radiation X.

When the radiation detecting cassette 24 is used in the medical examination room 12 or the like, the radiation detecting cassette 24 may be subjected to adhesion of blood, contamination, etc. However, when the radiation detecting cassette 24 is designed to have a waterproof and hermetically-sealed structure, and is sterilized and cleaned as necessary, one radiation detecting cassette 24 can be used repeatedly.

The radiation detecting cassette 24 is not limited to use in the medical examination room 12, and may be used for a medical examination and a round in the hospital.

Also, the radiation detecting cassette 24 may communicate with external devices via optical wireless communication using infrared light or the like, instead of general wireless communication using radio wave.

Figure 3:
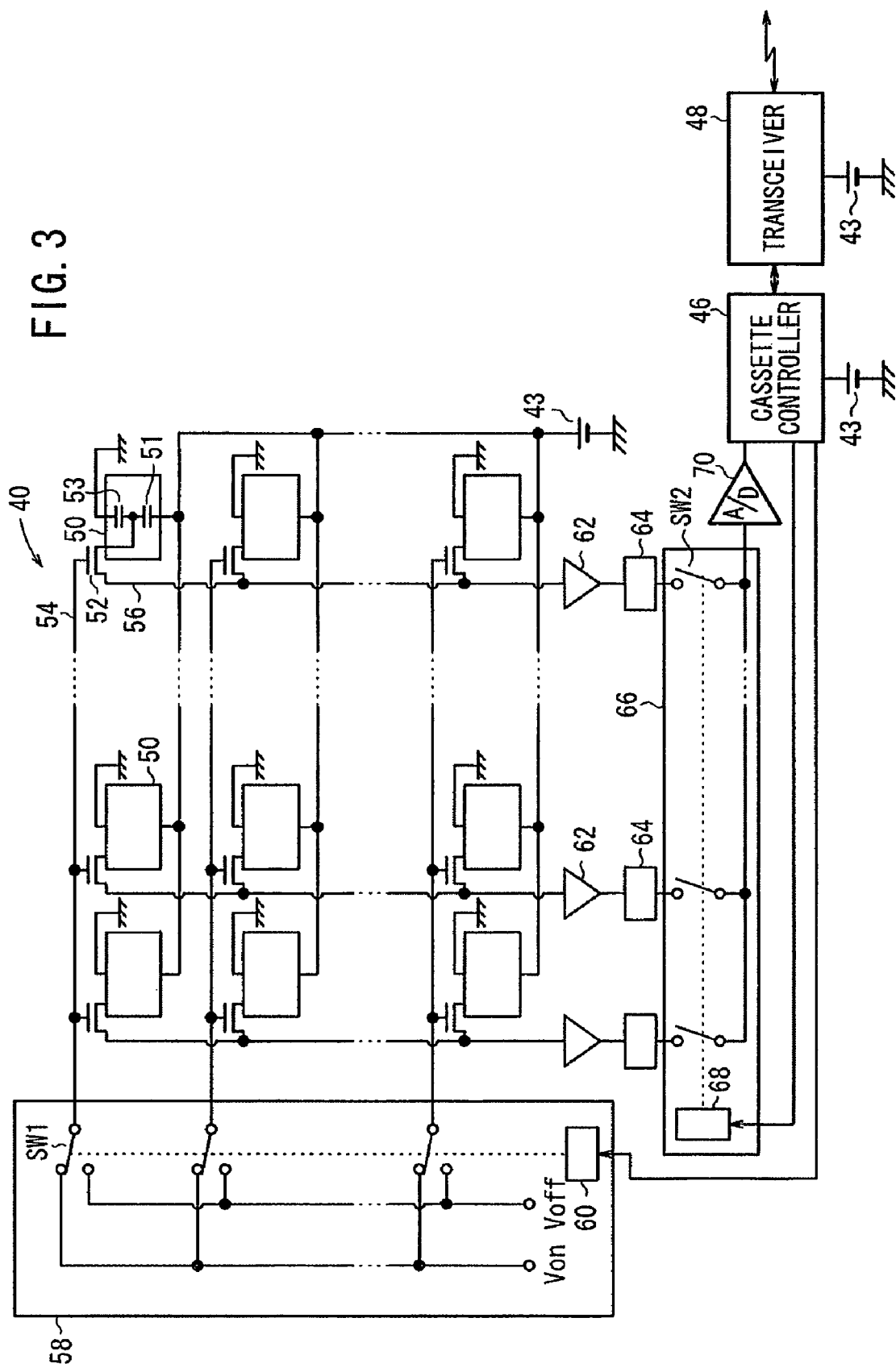
FIG. 3 is a block diagram of a circuit arrangement of a radiation detector.

(3) Radiation Detector:

FIG. 3 shows in block form a circuit arrangement of the radiation detector 40. As shown in FIG. 3, the radiation detector 40 comprises an array of thin-film transistors (TFTs) 52 arranged in rows and columns, a photoelectric conversion layer 51 made of a material such as amorphous selenium (a-Se) for generating electric charges upon detection of the radiation X, the photoelectric conversion layer 51 being disposed over the array of TFTs 52, and an array of storage capacitors 53 connected to the photoelectric conversion layer 51. When the radiation X is applied to the radiation detector 40, the photoelectric conversion layer 51 generates electric charges, and the storage capacitors 53 store the generated electric charges. Then, the TFTs 52 are successively turned on along each row at a time to read out the electric charges from the storage capacitors 53 as an image signal. In FIG. 3, the photoelectric conversion layer 51 and one of the storage capacitors 53 are shown as a pixel 50, and the pixel 50 is connected to one of the TFTs 52. Details of the other pixels 50 are omitted from illustration. Since amorphous selenium tends to change its structure and lose its functionality at high temperatures, amorphous selenium needs to be used within a certain temperature range. Therefore, some means for cooling the radiation detector 40 should preferably be provided in the cassette 24.

The TFTs 52 connected to the respective pixels 50 are connected to respective gate lines 54 extending parallel to the rows and respective signal lines 56 extending parallel to the columns. The gate lines 54 are connected to a line scanning driver 58, and the signal lines 56 are connected to a multiplexer 66 serving as a reading circuit.

The gate lines 54 are supplied with control signals Von, Voff from the line scanning driver 58 for turning on and off the TFTs 52 along the rows. The line scanning driver 58 comprises a plurality of switches SW1 for switching between the gate lines 54 and an address decoder 60 for outputting a selection signal for selecting one of the switches SW1 at a time. The address decoder 60 is supplied with an address signal from the cassette controller 46.

The signal lines 56 are supplied with electric charges stored in the storage capacitors 53 of the pixels 50 through the TFTs 52 arranged in the columns. The electric charges supplied to the signal lines 56 are amplified by amplifiers 62 connected respectively to the signal lines 56. The amplifiers 62 are connected through respective sample and hold circuits 64 to the multiplexer 66. The multiplexer 66 comprises a plurality of switches SW2 for successively switching between the signal lines 56 and an address decoder 68 for outputting a selection signal for selecting one of the switches SW2 at a time. The address decoder 68 is supplied with an address signal from the cassette controller 46. The multiplexer 66 has an output terminal connected to an A/D converter 70. A radiation image signal generated by the multiplexer 66 based on the electric charges from the sample and hold circuits 64 is converted by the A/D converter 70 into a digital image signal representing radiation image data, which is supplied to the cassette controller 46.

Figure 4:
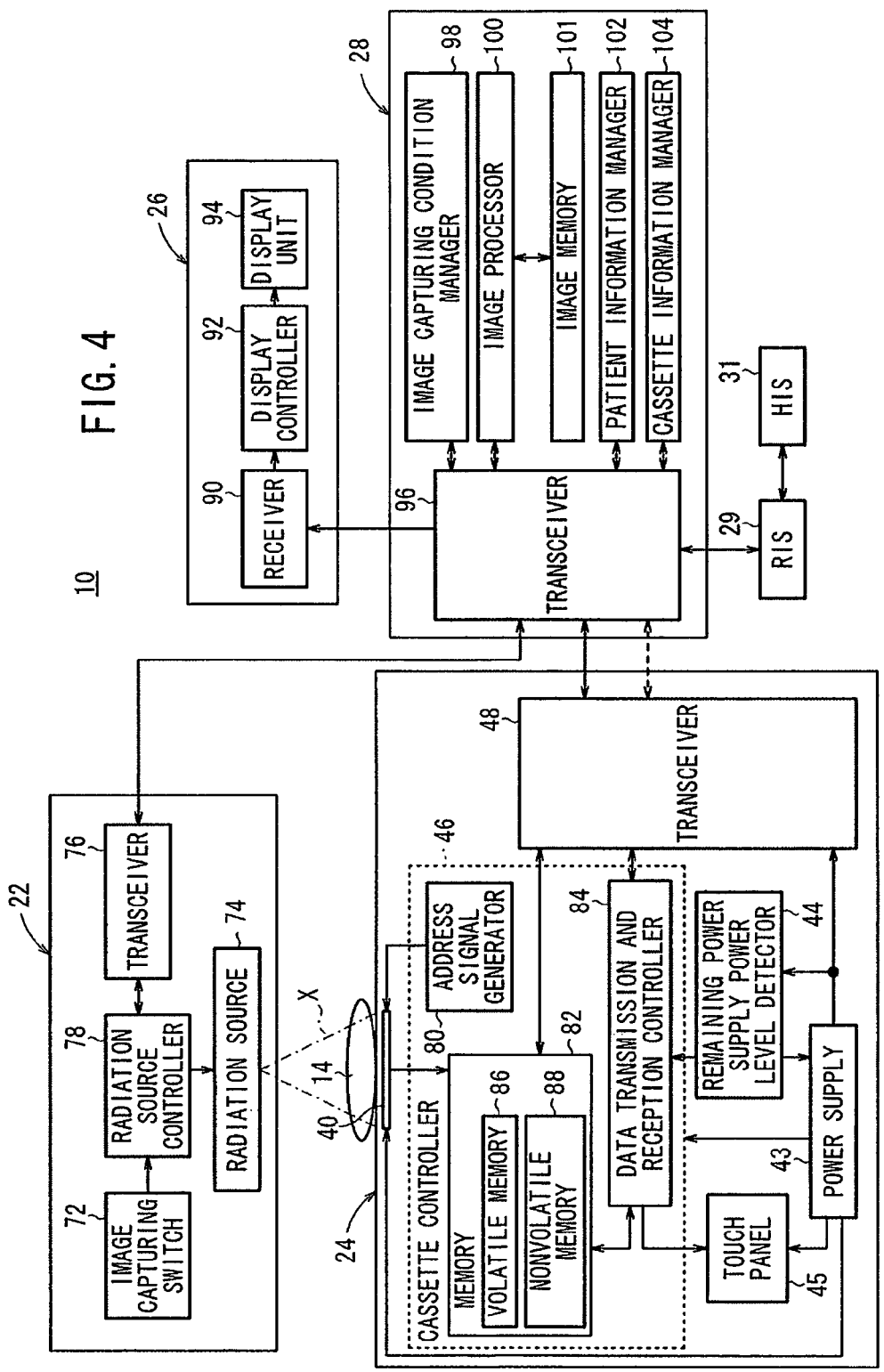
FIG. 4 is a block diagram of the radiation image capturing system according to the first embodiment of the present invention.

(4) Details of the Components:

FIG. 4 is a block diagram showing the components of the radiation image capturing system 10 which comprises the radiation irradiating device 22, the radiation detecting cassette 24, the display device 26, and the console 28. The console 28 is connected to a radiology information system (RIS) 29 which generally manages radiation image data handled by the radiological department of the hospital and other information. The RIS 29 is connected to a hospital information system (HIS) 31 which generally manages medical information in the hospital.

(a) Radiation Irradiating Device 22:

The radiation irradiating device 22 comprises an image capturing switch 72, a radiation source 74 for outputting the radiation X, a transceiver 76 for receiving image capturing conditions from the console 28 by way of wireless communications and transmitting a signal such as an image capturing completion signal, etc. to the console 28 by way of wireless communications, and a radiation source controller 78 for controlling the radiation source 74 based on an image capturing start signal supplied from the image capturing switch 72 and image capturing conditions supplied from the transceiver 76.

(b) Radiation Detecting Cassette 24:

The cassette 24 houses therein the radiation detector 40, the power supply 43, a remaining power supply power level detector 44, the cassette controller 46, the transceiver 48, and the touch panel 45. The power supply 43 energizes the radiation detector 40, the remaining power supply power level detector 44, the cassette controller 46, the transceiver 48, and the touch panel 45.

The cassette controller 46 comprises an address signal generator 80 for supplying address signals to the address decoder 60 of the line scanning driver 58 (FIG. 3) and the address decoder 68 of the multiplexer 66 of the radiation detector 40, a memory 82 for storing the radiation image data detected by the radiation detector 40 and cassette ID data for identifying the radiation detecting cassette 24, and a data transmission and reception controller 84 for controlling the transmission of radiation image data depending on the remaining power level RC (%) of the power supply 43 which is detected by the remaining power supply power level detector 44.

The memory 82 includes a volatile memory 86 for temporarily storing radiation image data and a nonvolatile memory 88 for permanently storing radiation image data and cassette ID data. The volatile memory 86 comprises a DRAM, for example. The volatile memory 86 loses its stored data when the power supplied from the power supply 43 is cut off. The nonvolatile memory 88 comprises a flash memory, for example. The nonvolatile memory 88 keeps radiation image data and cassette ID data stored therein even when the power supplied from the power supply 43 is cut off.

The transceiver 48 receives a transmission request signal for cassette ID data and radiation image data from the console 28 by way of wireless communications or wired communications, and transmits the cassette ID data stored in the nonvolatile memory 88 and the radiation image data stored in the volatile memory 86 or the nonvolatile memory 88, to the console 28 by way of wireless communications or wired communications.

The touch panel 45 is operated by the operator to enter various settings for the cassette 24, and displays messages for the operator.

(c) Display Device 26:

The display device 26 comprises a receiver 90 for receiving radiation image data from the console 28, a display controller 92 for controlling the display of the received radiation image data, and a display unit 94 for displaying the radiation image data processed by the display controller 92.

(d) Console 28:

The console 28 comprises a transceiver 96 for transmitting and receiving necessary information including radiation image data to and from the irradiating device 22, the radiation detecting cassette 24, and the display device 26 by way of wireless communications or wired communications, an image capturing condition manager 98 for managing image capturing conditions required for the irradiating device 22 to capture radiation images, an image processor 100 for processing radiation image data transmitted from the cassette 24, an image memory 101 for staring the processed radiation image data, a patient information manager 102 for managing patient information of the patient 14 whose images are to be captured, and a cassette information manager 104 for managing cassette information.

The image capturing conditions refer to conditions required for determining a tube voltage, a tube current, an irradiation time, etc. required to apply a radiation X at an appropriate dose to an area of the patient 14 to be imaged, and may be an area to be imaged, an image capturing method, etc. The image capturing conditions also include the number of radiation images to be captured. The patient information refers to information for identifying the patient 14 such as name, gender, age, patient ID, etc. Ordering information, including the image capturing conditions and the patient information, for instructing the radiation image capturing system 10 to capture radiation images of the patient 14 can be either directly prepared on the console 28 or supplied from an external source via the RIS 29 to the console 28.

The cassette information refers to the cassette ID data for identifying the cassette 24.

2. Operation of the First Embodiment:

The radiation image capturing system 10 according to the first embodiment is basically constructed as described above, and operation of the radiation image capturing system 10 will be described below with reference to FIGS. 5 and 6.

The radiation image capturing system 10 is installed in the medical examination room 12 and used when a radiation image of the patient 14 is required by the doctor 18 who is examining the patient 14. Before a radiation image of the patient 14 is captured, patient information of the patient 14 to be imaged is registered in the patient information manager 102 of the console 28. If an area to be imaged of the patient 14, an image capturing method, and the number of radiation images to be captured have already been known, they are registered as image capturing conditions in the image capturing condition manager 98. After the above preparatory process is finished, the doctor 18 examines the patient 14.

If a radiation image of the patient 14 is to be captured during the examination, then the console 28 is triggered by an image capturing start signal from the doctor 18 or the radiological technician in charge to transmit a reception acknowledgement request signal for requesting a reception acknowledgement within a predetermined range. The doctor 18 or the radiological technician in charge places the cassette 24 in a given position between the patient 14 and the examination table 16 with the irradiated surface 36 facing the irradiating device 22. When the cassette 24 receives the reception acknowledgement request signal from the console 28, the cassette 24 transmits a reception acknowledgement notice signal for noticing a reception acknowledgement to the console 28. A communication link is now established between the cassette 24 and the console 28 (step S1).

In step S2, the cassette 24 is triggered by the reception acknowledgement request signal from the console 28 to have the remaining power supply power level detector 44 detect the remaining power level RC of the power supply 43. In step S3, the cassette controller 46 selects a method of handling the radiation image data based on the detected remaining power level RC. Available methods of handling the radiation image data to choose from include transmitting the radiation image data by way of wireless communications ("wireless transmission"), transmitting the radiation image data by way of wired communications ("wired transmission"), and saving the radiation image data in the nonvolatile memory ("saving in the nonvolatile memory 88").

Figure 5:
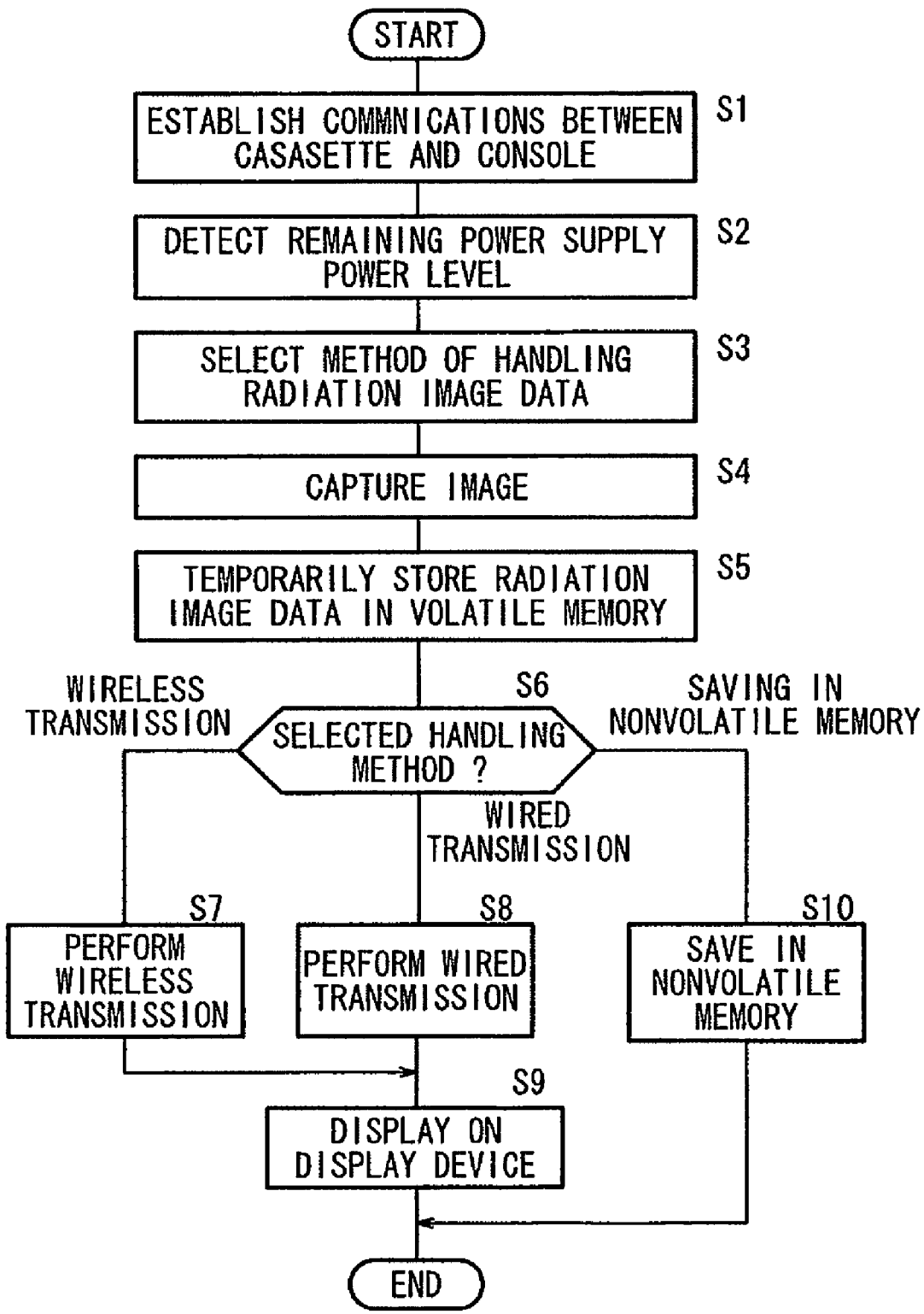
FIG. 5 is a flowchart of an operation sequence of the radiation image capturing system according to the first embodiment of the present invention.
Figure 6:
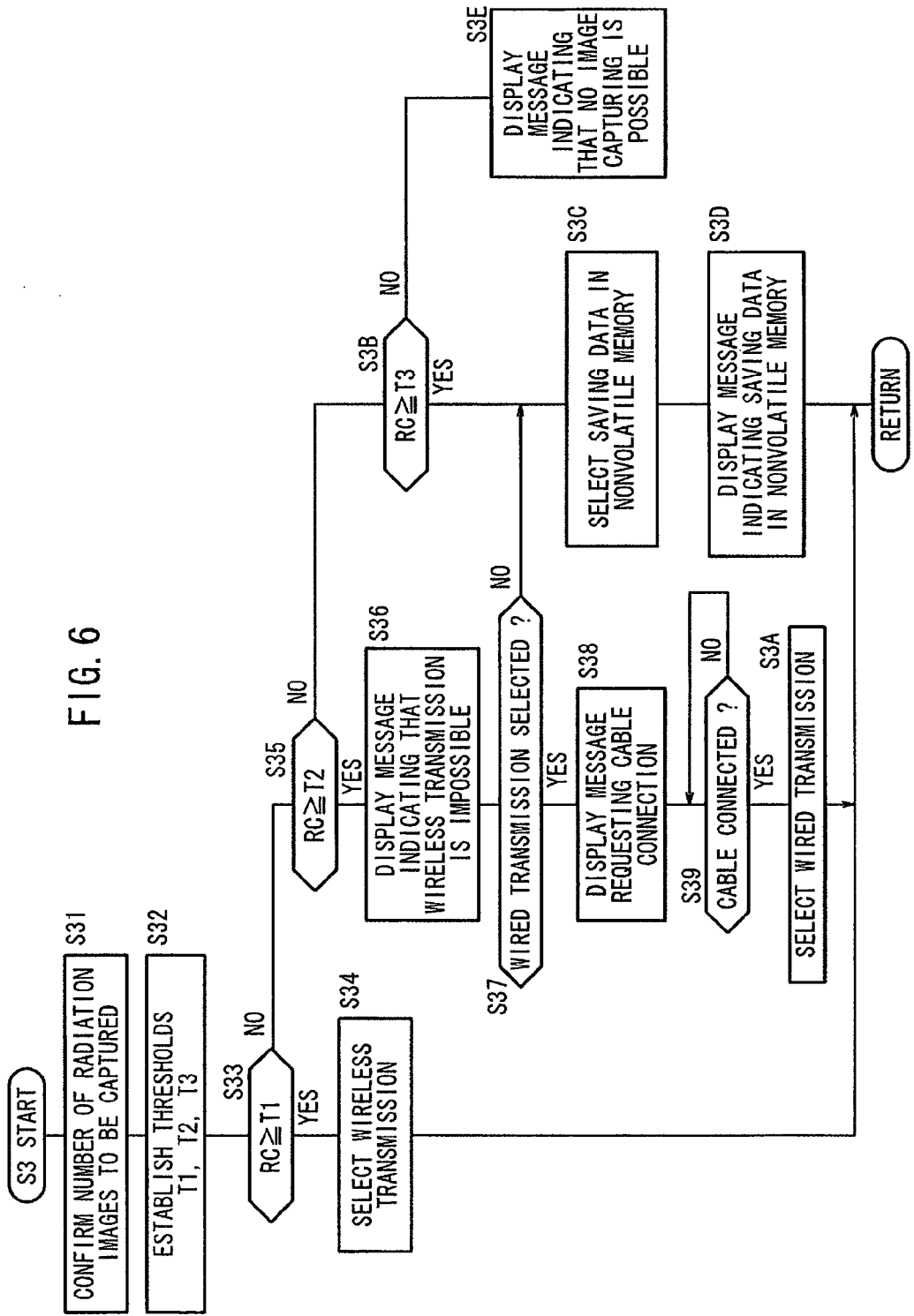
FIG. 6 is a flowchart showing details of a subroutine of the operation sequence shown in FIG. 5.

FIG. 6 is a flowchart showing details of step S3 of the operation sequence shown in FIG. 5. In step S31, the cassette controller 46 confirms the number of radiation images to be captured. Specifically, the data transmission and reception controller 84 of the cassette controller 46 sends an image count inquiry signal for inquiring the number of radiation images to be captured to the image capturing condition manager 98 of the console 28. In response to the image count inquiry signal, the image capturing condition manager 98 returns an image count notice signal for noticing the number of radiation images to be captured to the data transmission and reception controller 84. The cassette controller 46 confirms the number of radiation images to be captured from the image count notice signal.

In step S32, the data transmission and reception controller 84 of the cassette controller 46 establishes thresholds T1, T2, T3 (%) (T1>T2>T3) for the remaining power level RC of the power supply 43 depending on the number of radiation images to be captured. The thresholds T1, T2, T3 represent proportions with respect to the maximum value (100%) of the remaining power level RC of the power supply 43. The threshold T1 represents a minimum value of the remaining power level RC which is capable of transmitting all the radiation image data depending on the number of radiation images to be captured by way of wireless communications. The threshold T2 represents a minimum value of the remaining power level RC which is incapable of transmitting some of the radiation image data depending on the number of radiation images to be captured by way of wireless communications, but is capable of transmitting all the radiation image data by way of wired communications. The threshold T3 represents a minimum value of the remaining power level RC which is incapable of transmitting the radiation image data by way of wireless and wired communications, but is capable of saving the radiation image data in the nonvolatile memory 88. If the remaining power level RC is lower than the threshold T3, then no radiation images can be captured. The thresholds T1, T2, T3 can be calculated by determining, in advance, values of the remaining power level RC that are required to transmit the radiation image data representing, e.g., one radiation image to be captured by way of wireless communications and wired communications and to save the radiation image data in the nonvolatile memory 88, and multiplying the determined values by the number of radiation images to be captured. Alternatively, values of the remaining power level RC that are required to transmit the radiation image data by way of wireless communications and wired communications and to save the radiation image data in the nonvolatile memory 88 may be calculated in advance for the respective numbers of radiation images to be captured.

In step S33, the data transmission and reception controller 84 determines whether or not the remaining power level RC detected by the remaining power supply power level detector 44 is equal to or greater than the threshold T1. If the remaining power level RC is equal to or greater than the threshold T1, then the cassette controller 46 selects "wireless transmission" as the method of handling the radiation image data in step S34. If the remaining power level RC is smaller than the threshold T1, then control goes to step S35.

In step S35, the data transmission and reception controller 84 determines whether or not the remaining power level RC detected by the remaining power supply power level detector 44 is equal to or greater than the threshold T2. If the remaining power level RC is equal to or greater than the threshold T2, then the cassette controller 46 displays, on the touch panel 45, a message indicating that the remaining power level RC is running low and the radiation image data cannot be transmitted by way of wireless communications, in step S36. In step S37, the cassette controller 46 displays, on the touch panel 45, a message prompting the operator to select either transmitting the radiation image data by way of wired communications or saving the radiation image data in the nonvolatile memory 88.

If the operator selects transmitting the radiation image data by way of wired communications in step S37, the data transmission and reception controller 84 displays a message prompting the operator to connect the cable 49 on the touch panel 45 in step S38, and then monitors whether the cable 49 is connected or not until the cable 49 is actually connected in step S39. If the cable 49 is connected, then the cassette controller 46 selects "wired transmission" as the method of handling the radiation image data in step S3A.

If the operator selects saving the radiation image data in the nonvolatile memory 88 in step S37, then control goes to step S3C to be described later.

If the remaining power level RC is smaller than the threshold T2 in step S35, then the data transmission and reception controller 84 determines whether or not the remaining power level RC detected by the remaining power supply power level detector 44 is equal to or greater than the threshold T3 in step S3B. If the remaining power level RC is equal to or greater than the threshold T3, then the data transmission and reception controller 84 selects "saving in the nonvolatile memory 88" as the method of handling the radiation image data in step S3C. Then, the data transmission and reception controller 84 displays, on the touch panel 45, a message indicating that the method of "saving in the nonvolatile memory 88" is selected, i.e., the radiation image data are saved in the cassette 24, in step S3D. At this time, the message may also be sent via the console 28 to the display device 26 and displayed thereon. In addition, the cassette 24 indicates, to the console 28, that "saving in the nonvolatile memory 88" is selected as the method of handling the radiation image data. The console 28 now recognizes that no radiation image data are transmitted from the cassette 24 at the moment.

If the remaining power level RC is smaller than the threshold T3 in step S3B, then the cassette controller 46 displays, on the touch panel 45, a message indicating that no radiation image data can be acquired in step S3E.

Referring back to FIG. 5, after the method of handling the radiation image data is selected in step S3, the doctor 18 moves the irradiating device 22 to a position confronting the cassette 24, and then turns on the image capturing switch 72 to capture a radiation image of the patient 14 in step S4.

On capturing the image, the radiation source controller 78 of the irradiating device 22 acquires the image capturing conditions for the area to be imaged of the patient 14 from the image capturing condition manager 98 of the console 28 via the transceivers 96, 76. According to the acquired image capturing conditions, the radiation source controller 78 controls the radiation source 74 to apply a radiation X at a given dose to the patient 14.

The radiation X which has passed through the patient 14 is applied to the grid 38 of the radiation detecting cassette 24, which removes scattered rays of the radiation X. Then, the radiation X is applied to the radiation detector 40, and converted into electric signals by the photoelectric conversion layer 51 of the pixels 50 of the radiation detector 40. The electric signals are stored as electric charges in the storage capacitors 53 (see FIG. 3). The stored electric charges in the storage capacitors 53, which represent the radiation image data of the patient 14, are read out from the storage capacitors 53 according to address signals which are supplied from the address signal generator 80 of the cassette controller 46 to the line scanning driver 58 and the multiplexer 66.

Specifically, in response to the address signal supplied from the address signal generator 80, the address decoder 60 of the line scanning driver 58 outputs a selection signal to select one of the switches SW1, which supplies the control signal Von to the gates of the TFTs 52 connected to the gate line 54 corresponding to the selected switch SW1. In response to the address signal supplied from the address signal generator 80, the address decoder 68 of the multiplexer 66 outputs a selection signal to successively turn on the switches SW2 to switch between the signal lines 56 for thereby reading out the electric charges stored in the storage capacitors 53 of the pixels 50 connected to the selected gate line 54, through the signal lines 56.

In step S5, the cassette controller 46 temporarily records the radiation image data in the volatile memory 86. Specifically, the electric charges read out from the storage capacitors 53 of the respective pixels 50 connected to the selected gate line 54 of the radiation detector 40 are amplified by the respective amplifiers 62, sampled by the sample and hold circuits 64, and supplied to the multiplexer 66. Based on the supplied electric charges, the multiplexer 66 generates and supplies a radiation image signal to the A/D converter 70, which converts the radiation image signal into a digital signal. The digital signal which represents the radiation image data is temporarily stored in the volatile memory 86 of the cassette controller 46.

Similarly, the address decoder 60 of the line scanning driver 58 successively turns on the switches SW1 to switch between the gate lines 54 according to the address signal supplied from the address signal generator 80. The electric charges stored in the storage capacitors 53 of the pixels 50 connected to the successively selected gate lines 54 are read out through the signal lines 56, and processed by the multiplexer 66 and the A/D converter 70 into digital signals, which are stored in the volatile memory 86 of the cassette controller 46.

In step S6, the cassette controller 46 confirms the handling method selected in step S3. If the wireless transmission is selected in step S3, then the cassette controller 46 transmits the radiation image data to the console 28 by way of wireless communications in step S7. If the wired transmission is selected in step S3, then the cassette controller 46 sends the radiation image data to the console 28 by way of wired communications in step S8.

When the wireless transmission is performed in step S7 or the wired transmission is performed in step S8, the radiation image data are displayed on the display device 26 in step S9. Specifically, the radiation image data transmitted from the cassette 24 to the console 28 are received by the transceiver 96, processed by the image processor 100, and then stored in the image memory 101 in association with the patient information of the patient 14 registered in the patient information manager 102. The radiation image data processed by the image processor 100 are transmitted from the transceiver 96 to the display device 26. In the display device 26, the receiver 90 receives the radiation image data, and the display controller 92 controls the display unit 94 to display a radiation image based on the radiation image data. The doctor 18 examines the patient 14 while watching the radiation image displayed on the display unit 94.

Since no cables 49 for transmitting and receiving signals are connected between the cassette 24 and the console 28, it is not necessary to lay such cables 49 on the floor of the medical examination room 12 and hence there are no cable-induced obstacles to the examination performed by the doctor 18, the radiological technician, or other staff members in the medical examination room 12.

If the saving in the nonvolatile memory 88 is selected in step S3, then the cassette controller 46 does not transmit the radiation image data to the console 28, but saves the radiation image data in the nonvolatile memory 88 in step S10. After the remaining power level RC of the power supply 43 is increased by recharging the power supply 43 of the cassette 24 or replacing it with a new one, or connecting a power supply cable, not shown, to the cassette 24, then the radiation image data saved in the nonvolatile memory 88 can be transmitted to the console 28.

3. Advantages of the First Embodiment

According to the first embodiment, as described above, when the remaining power level RC of the power supply 43 becomes lower than the threshold T1, the data transmission and reception controller 84 of the cassette controller 46 stops the wireless transmission of radiation image data and prioritizes the capturing of a radiation image. Therefore, when the remaining power level RC of the power supply 43 runs low, the electric power is preferentially supplied to capture a radiation image. The low remaining power level RC is thus effectively used to acquire radiation image data.

According to the first embodiment, the threshold T1 is variable. The amount of electric power required to capture a radiation image and transmit radiation image data by way of wireless communications changes depending on the number of radiation images to be captured or the like. It is possible to set the threshold T1 to a value in view of the required amount of electric power.

When the wireless and wired transmission of radiation image data is stopped, the data transmission and reception controller 84 stores the radiation image data in the nonvolatile memory 88. Accordingly, even when the power supply 43 of the cassette 24 is turned off, the radiation image data remain stored in the nonvolatile memory 88, and the time to transmit the radiation image data to the console 28 can be determined as desired. The radiation detecting cassette 24 can thus be used conveniently.

When the remaining power level RC of the power supply 43 becomes lower than the threshold T1 and is equal or greater than the threshold T2, the data transmission and reception controller 84 transmits radiation image data to the console 28 by way of wired communications. Since wired communications generally consume less electric power than wireless communications, even if the remaining power level RC of the power supply 43 is not high enough to transmit radiation image data by way of wireless communications, the radiation image data can be transmitted by way of wired communications. Therefore, radiation image data can be transmitted to an external device earlier than if the transmission of the radiation image data is canceled at all times when the wireless transmission is impossible. Consequently, the radiation detecting cassette 24 can be used conveniently.

B. 2nd Embodiment

Figure 7:
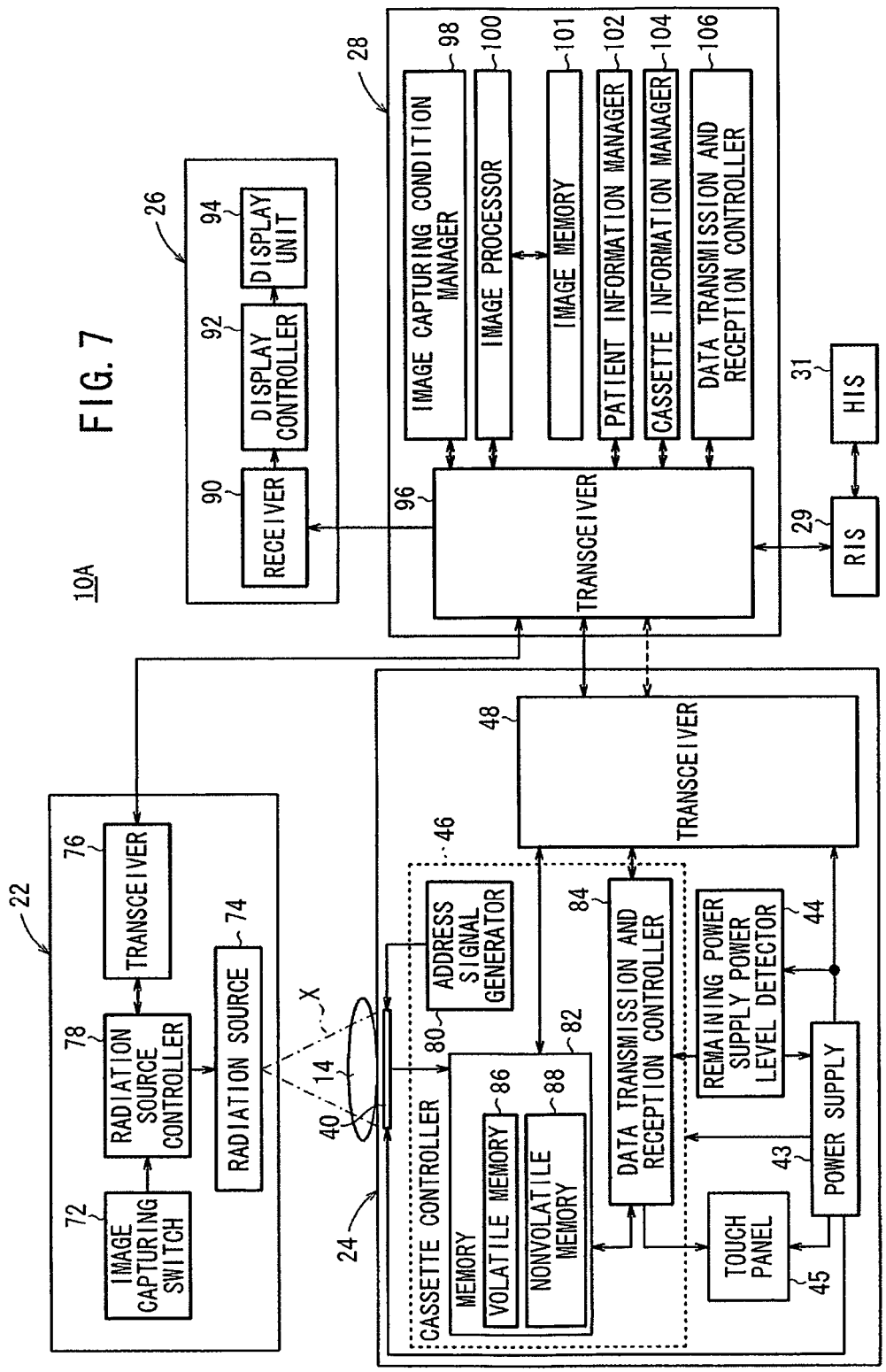
FIG. 7 is a block diagram of a radiation image capturing system according to a second embodiment of the present invention.

1. Configuration of Radiation Image Capturing System 10A (Differences from the First Embodiment):

FIG. 7 shows in block form a radiation image capturing system 10A (hereinafter also referred to as "image capturing system 10A") according to a second embodiment of the present invention. The image capturing system 10A according to the second embodiment is basically the same as the image capturing system 10 according to the first embodiment. However, the image capturing system 10A differs from the image capturing system 10 in that the console 28, rather than the cassette 24, selects a method of handling the radiation image data, i.e., "wireless transmission", "wired transmission", or "saving in the nonvolatile memory 88". Specifically, in the image capturing system 10A, the console 28 includes a data transmission and reception controller 106, and the data transmission and reception controller 106 of the console 28, rather than the data transmission and reception controller 84 of the cassette 24, selects a method of handling the radiation image data (step S3 shown in FIG. 5 and steps S31 through S3E shown in FIG. 6). The display unit 94 of the display device 26, rather than the touch panel 45 of the cassette 24, displays messages (steps S36, S38, S3D shown in FIG. 6). The data transmission and reception controller 84 of the cassette 24 transmits the remaining power level RC detected by the remaining power supply power level detector 44 to the console 28, receives information about the method of handling the radiation image data selected by the console 28, and performs the subsequent process according to the selected handling method. Those parts of the image capturing system 10A which are identical to those of the image capturing system 10 are denoted by identical reference characters, and will not be described below.

2. Advantages of the Second Embodiment

According to the second embodiment, as described above, the console 28, rather than the cassette 24, selects a method of handling the radiation image data. Therefore, the burden on the processing sequence of the cassette 24 is reduced, making it possible to simplify the circuit arrangement of the cassette 24. As the cassette 24 often needs to change its position depending on the area of the patient 14 to be imaged, the cassette 24 is more required to be reduced in weight and increased in durability than the console 28. The simpler circuit arrangement of the cassette 24 leads to an increase in the overall performance of the image capturing system 10A.

C. 3rd Embodiment

Figure 8:
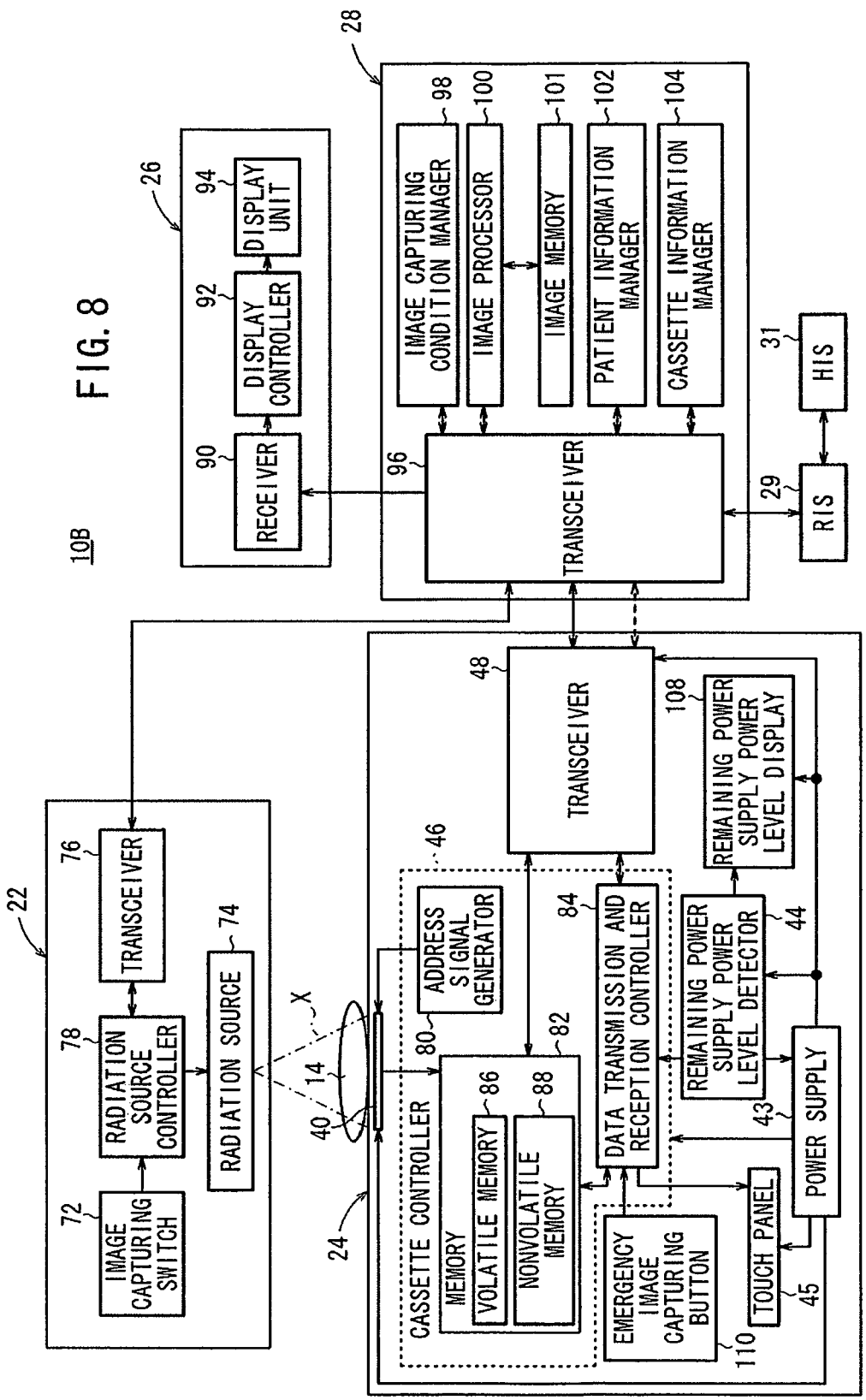
FIG. 8 is a block diagram of a radiation image capturing system according to a third embodiment of the present invention.

1. Configuration of Radiation Image Capturing System 10B (Differences from the First Embodiment):

FIG. 8 shows in block form a radiation image capturing system 10B (hereinafter also referred to as "image capturing system 10B") according to a third embodiment of the present invention. The image capturing system 10B according to the third embodiment is basically the same as the image capturing system 10 according to the first embodiment. However, the image capturing system 10B differs from the image capturing system 10 in that it is arranged to keep a certain remaining power level RC of the power supply 43 for capturing radiation images in emergency. Specifically, in the image capturing system 10B, the cassette 24 has a remaining power supply power level display 108 for displaying the remaining power level RC detected by the remaining power supply power level detector 44. When the remaining power level RC of the power supply 43 drops to a provisional empty value Ep, the remaining power supply power level display 108 displays that the remaining power level RC is nil. The provisional empty value Ep may be set to a remaining power level RC which is capable of acquiring radiation image data of at least one radiation image. According to the present invention, the remaining power level RC which is capable of acquiring radiation image data of 10 radiation images is used as the provisional empty value Ep.

When the remaining power level RC of the power supply 43 drops to the provisional empty value Ep, the data transmission and reception controller 84 of the cassette controller 46 instructs the power supply 43 to inhibit its electric power from being supplied to the radiation detector 40. When the power supply 43 is so instructed, it turns off a switch, not shown, to stop supplying its electric power to the radiation detector 40.

The cassette 24 also has an emergency image capturing button 110 for capturing radiation images in emergency. Even when the remaining power level RC drops to the provisional empty value Ep, if the operator presses the emergency image capturing button 110, i.e., if the operator gives an instruction to supply electric power, the data transmission and reception controller 84 instructs the power supply 43 to supply its electric power to the radiation detector 40. When the power supply 43 is so instructed, it turns on the switch or another process is made to resume supplying its electric power to the radiation detector 40, and continues to supply its electric power to the radiation detector 40 until the remaining power level RC of the power supply 43 becomes completely nil.

2. Advantages of the Third Embodiment:

According to the third embodiment, as described above, when the remaining power level RC of the power supply 43 drops to the provisional empty value Ep, which is not actually nil, the remaining power supply power level display 108 displays that the remaining power level RC is nil, for thereby warning the operator to stop acquiring radiation image data. As a result, the remaining power of the power supply 43 is kept at a level at which radiation image data of at least one radiation image can be acquired. Therefore, the image capturing system 10B can easily meet demands for the acquisition of radiation image data in emergency. Inasmuch as the operator is notified of a reduction in the remaining power level RC of the power supply 43, the operator is prompted to recharge the power supply 43, which thus minimizes its undue deterioration.

When the remaining power level RC of the power supply 43 drops to the provisional empty value Ep, the data transmission and reception controller 84 inhibits the power supply 43 from supplying its electric power to the radiation detector 40. When the emergency image capturing button 110 is pressed, the data transmission and reception controller 84 permits the power supply 43 to supply its electric power to the radiation detector 40. Accordingly, the remaining power of the power supply 43 is reliably kept at a level at which radiation image data of at least one radiation image can be acquired, and the image capturing system 10B can easily meet demands for the acquisition of radiation image data in emergency.

D. Modifications

The present invention is not limited to the above embodiments, but various changes and modifications may be made therein as indicated by (1) through (5) shown below.

1. Radiation Image Capturing Systems 10, 10A, 10B:

In each of the above embodiments, the image capturing systems 10, 10A, 10B are placed in the medical examination room 12. However, the image capturing systems 10, 10A, 10B may be a movable system for use in visiting hospital rooms. The image capturing systems 10, 10A, 10B may not movable, but may be fixedly placed in position.

In each of the above embodiments, the image capturing system 10 is connected to the RIS 29. However, the image capturing system 10 may be used alone. If the image capturing system 10 is used alone, then cassette IDs and patient IDs may be input directly to the console 28.

2. Radiation Conversion Panel (Radiation Detector 40):

In each of the above embodiments, the radiation detector 40 housed in the radiation detecting cassette 24 directly converts the dose of the applied radiation X into an electric signal with the photoelectric conversion layer 51. However, the radiation image capturing system may employ a radiation detector including a scintillator for converting the applied radiation X into visible light and a solid-state detecting device such as of amorphous silicon (a-Si) or the like for converting the visible light into an electric signal (see Japanese Patent No. 3494683).

Alternatively, the radiation image capturing system may employ a light-conversion radiation detector for acquiring radiation image data. The light-conversion radiation detector operates as follows: When a radiation is applied to a matrix of solid-state detecting devices, the solid-state detecting devices store an electrostatic latent image depending on the dose of the applied radiation. For reading the stored electrostatic latent image, reading light is applied to the solid-state detecting devices to cause the solid-state detecting devices to generate an electric current representing radiation image data. When erasing light is applied to the radiation detector, radiation image data representing a residual electrostatic latent image are erased from the radiation detector, which can thus be reused (see Japanese Laid-Open Patent Publication No. 2000-105297).

3. Power Supply 43 and Remaining Power Supply Power Level Detector 44:

In each of the above embodiments, the radiation detector 40, the remaining power supply power level detector 44, the touch panel 45, the cassette controller 46, and the transceiver 48 are energized by the single power supply 43. However, they may be energized by a plurality of power supplies. In such a case, one or more remaining power supply power level detectors 44 may be provided for detecting the remaining power level RC of the power supply for energizing the radiation detector 40 and the remaining power level RC of the power supply for energizing the transceiver 48.

4. Thresholds T1, T2, T3:

In each of the above embodiments, the thresholds T1, T2, T3 are established depending on the number of radiation images to be captured. However, a resolution, a sensitivity, or the like may be used as an element based on which to establish the thresholds T1, T2, T3. It is also possible not to use either one of the thresholds T1, T2, T3.

5. Others:

In each of the above embodiments, the console 28 is located inside the medical examination room 12. However, the console 28 may be located outside of the medical examination room 12 insofar as it can transmit and receive signals to and from the irradiating device 22, the radiation detecting cassette 24, and the display device 26 by way of wireless communications.

In each of the above embodiments, the cassette controller 46 stores radiation image data in the nonvolatile memory 88 when it is not transmitting the radiation image data by way of wireless communications and wired communications. However, the cassette controller 46 may not need to store radiation image data in the nonvolatile memory 88 when it is not transmitting the radiation image data. For example, the cassette controller 46 may temporarily store the radiation image data in the volatile memory 86, supply electric power from an external power supply to the radiation detecting cassette 24 while the radiation image data are being stored in the volatile memory 86, and subsequently transmit the radiation image data with the supplied electric power by way of wireless communications.

In each of the above embodiments, the cassette controller 46 stores radiation image data temporarily in the volatile memory 86. However, if the radiation image data are transmitted at a high rate via the transceiver 48 by way of wireless communications or if the radiation image data are stored at a high rate in the nonvolatile memory 88, then the volatile memory 86 may be dispensed with.

In each of the above embodiments, radiation image data are transmitted by way of wired communications as well as wireless communications. However, wired communications or wireless communications may not be used to transmit radiation image data.

In each of the above embodiments, when radiation image data are not transmitted by way of wired communications or wireless communications, but stored in the nonvolatile memory 88 of the cassette 24, the touch panel 45 of the cassette 24 displays a message indicating that the radiation image data are not transmitted by way of wired communications or wireless communications. However, the cassette 24 may have an LED for indicating that radiation image data are being transmitted by way of wired communications or wireless communications, or an LED for indicating that radiation image data are being stored in the nonvolatile memory 88, and a selected method of handling the radiation image data may be indicated by the way in which the LED emits light or a change in the color of the light emitted by the LED.

In the third embodiment, when the remaining power level RC of the power supply 43 drops to the provisional empty value Ep, the power supply 43 stops supplying its electric power to the radiation detector 40. However, the power supply 43 may continuously supply its electric power to the radiation detector 40 whereas the remaining power supply power level display 108 displays that the remaining power level RC is nil.

Figure 9:
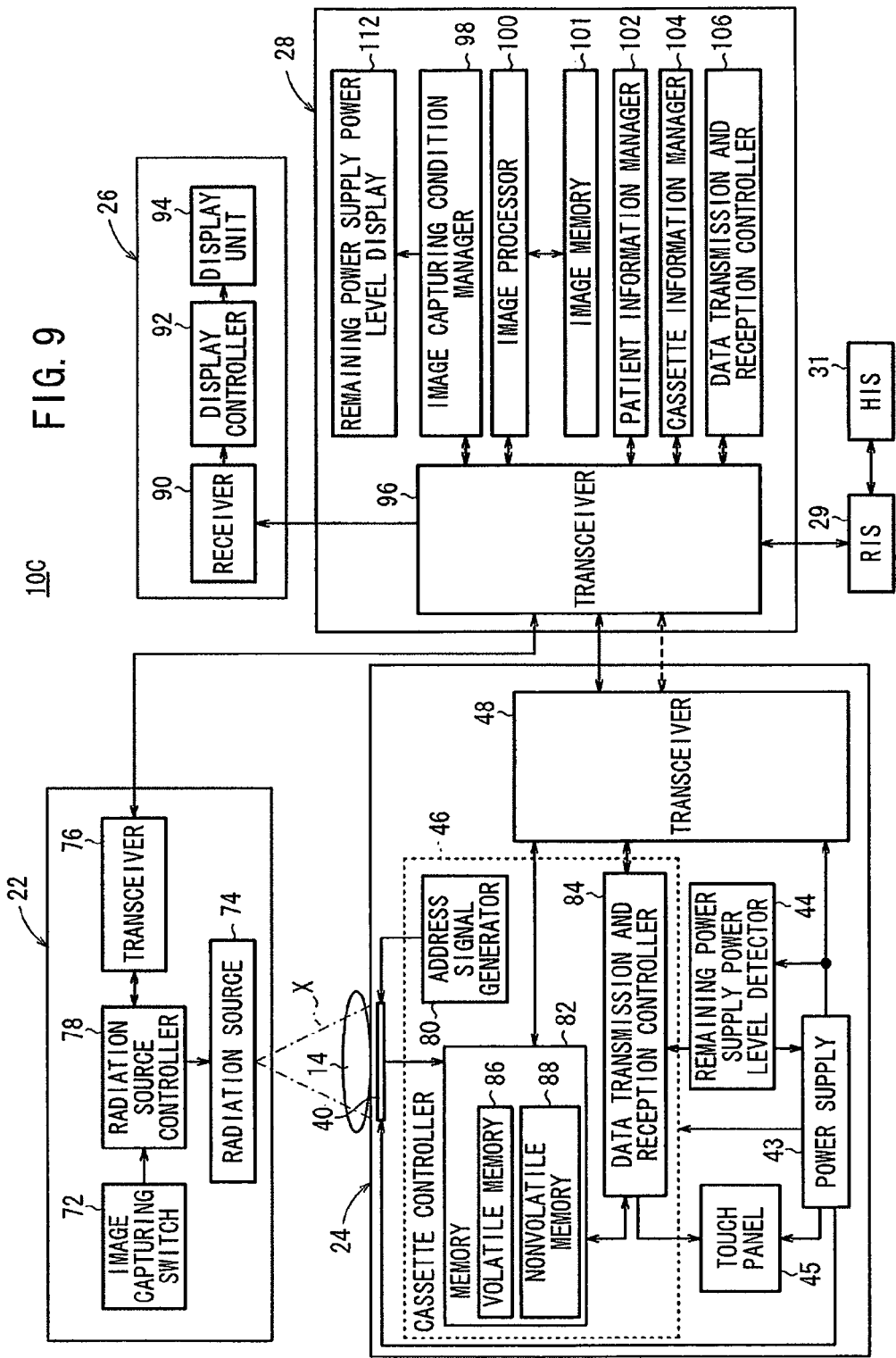
FIG. 9 is a block diagram of a modification of the radiation image capturing system according to the third embodiment of the present invention.

In the third embodiment, the cassette 24 itself keeps a certain remaining power level RC of the power supply 43 for capturing radiation images in emergency. However, a modified arrangement may be employed to keep a certain remaining power level RC of the power supply 43 for capturing radiation images in emergency. FIG. 9 shows in block form a modified radiation image capturing system 100 (hereinafter also referred to as "image capturing system 100") according to the present invention. In the radiation image capturing system 100, the cassette 24 and the console 28 are involved to keep a certain remaining power level RC of the power supply 43 for capturing radiation images in emergency. The remaining power level RC of the power supply 43 which is detected by the remaining power supply power level detector 44 of the cassette 24 is sent through the data transmission and reception controller 84, the transceiver 48, and the transceiver 96 to the image capturing condition manager 98 of the console 28, which displays the remaining power level RC on a remaining power supply power level display 112 of the console 28. The remaining power supply power level display 112 displays that the remaining power level RC is nil when the remaining power level RC of the power supply 43 drops to the provisional empty value Ep.

When the remaining power level RC of the power supply 43 drops to the provisional empty value Ep, the image capturing condition manager 98 instructs the data transmission and reception controller 84 to inhibit the power supply 43 from supplying its electric power to the radiation detector 40. The data transmission and reception controller 84 thus instructed controls the power supply 43 to stop supplying its electric power to the radiation detector 40.

The console 28 can be supplied with an emergency image capturing command Ce from a keyboard or the like, not shown. When the operator enters the emergency image capturing command Ce to the console 28 using the keyboard or the like, the image capturing condition manager 98 instructs the data transmission and reception controller 84 to control the power supply 43 to supply electric power to the radiation detector 40 even if the remaining power level RC is equal to or lower than the provisional empty value Ep. The data transmission and reception controller 84 thus instructed controls the power supply 43 to resume supplying its electric power to the radiation detector 40, and continue to supply its electric power to the radiation detector 40 until the remaining power level RC of the power supply 43 becomes completely nil.

Since the radiation image capturing system 10C does not need to have the remaining power supply power level display 108 and the emergency image capturing button 110 on the cassette 24, the radiation image capturing system 10C has further advantages in that the cassette 24 may be smaller in size and weight, in addition to the advantages described above with respect to the third embodiment.

Figure 10:
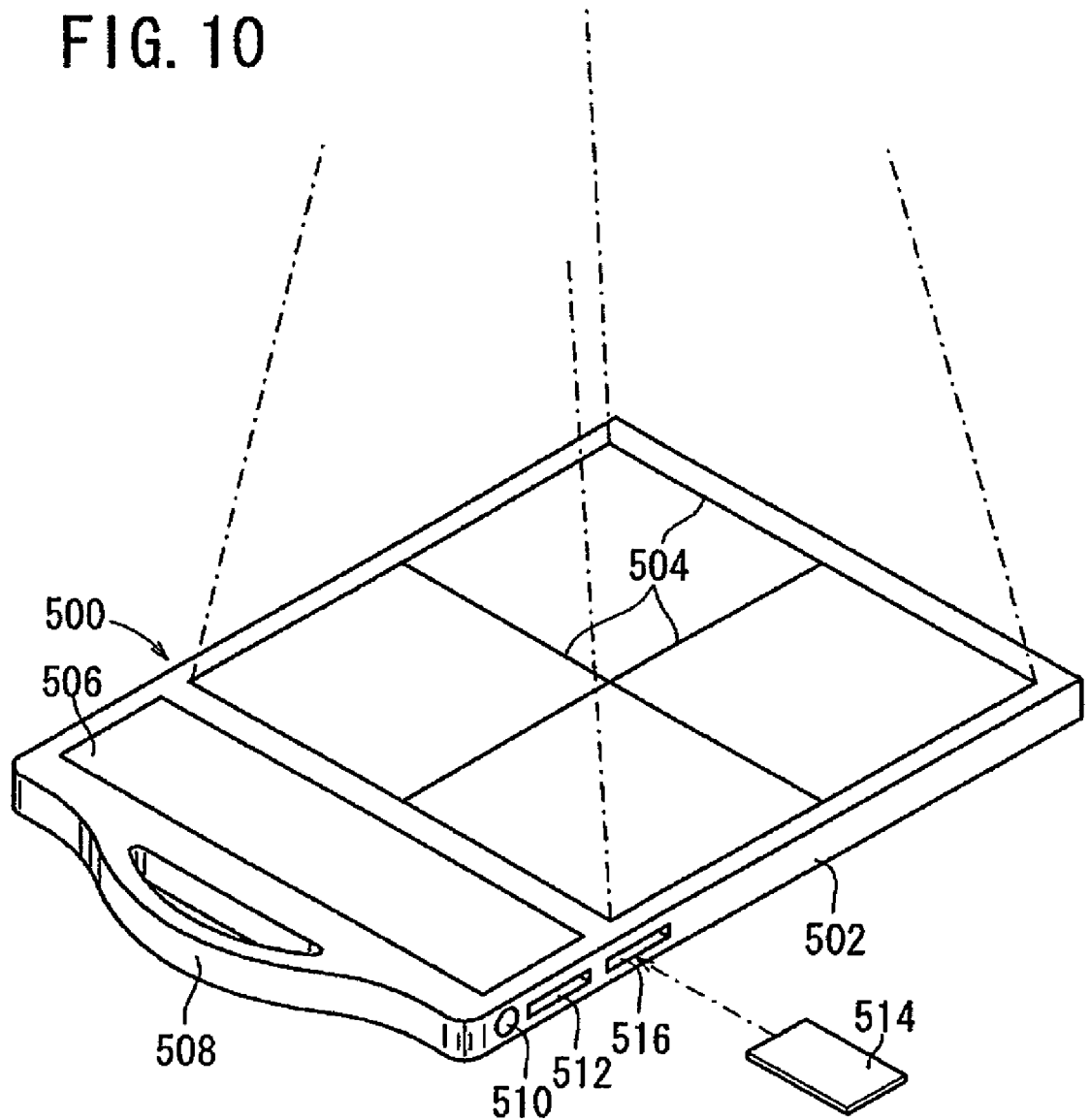
FIG. 10 is a perspective view showing a radiation detecting cassette according to another arrangement of the present invention.

Preferably, the radiation detecting cassette 500 (hereinafter referred to as "cassette 500") may be constructed as shown in FIG. 10.

Specifically, the cassette 500 includes a guiding line 504 drawn on the radiation-irradiated surface of a casing 502, the guiding line 504 serving as a reference for setting a captured area and a captured position. Using the guiding line 504, a subject (patient 14) can be positioned with respect to the cassette 500, and an area irradiated with the radiation X can be set, thereby recording radiation image information on an appropriate captured area.

The cassette 500 is provided with a display section 506 on an area thereof other than the captured area, for displaying various information about the cassette 500. The information which is displayed on the display section 506, includes ID information of the patient 14 whose radiation image information is to be recorded on the cassette 500, the number of times the cassette 500 has been used, an accumulated exposed radiation dose, a charging state (remaining level) of a power supply 43 in the cassette 500, image capturing conditions of radiation image information, and a positioning image of the patient 14 with respect to the cassette 500. In this case, a technician confirms the patient 14 based on the ID information displayed on the display section 506, for example, and also previously confirms that the cassette 500 is placed in a usable state. Then, the technician positions a desired captured area of the patient 14 with respect to the cassette 500 based on the displayed positioning image, thereby capturing appropriate radiation image information.

Also, the cassette 500 is provided with a handgrip 508, whereby it is easier to handle and carry the cassette 500.

Preferably, the cassette 500 may have, on a side thereof, an input terminal 510 for an AC adapter, a USB (Universal Serial Bus) terminal 512, and a card slot 516 for inserting a memory card 514.

When the charging function of the power supply 43 in the cassette 500 becomes deteriorated, or when there is not enough time to fully charge the power supply 43, the input terminal 510 is connected to the AC adapter to externally supply the cassette 500 with electric power, thereby enabling the cassette 500 to be used immediately.

The USB terminal 512 or the card slot 516 may be used when the cassette 500 cannot transmit and receive information to and from external devices such as the console 28 via wireless communication. Specifically, by connecting a cable to the USB terminal 512, the cassette 500 can transmit and receive information to and from the external devices via wire communication. Alternatively, the memory card 514 is inserted into the card slot 516, and necessary information is recorded on the memory card 514. After that, the memory card 514 is removed from the card slot 516, and the memory card 514 is inserted into the external device, thereby enabling information to be transferred.

Figure 11:
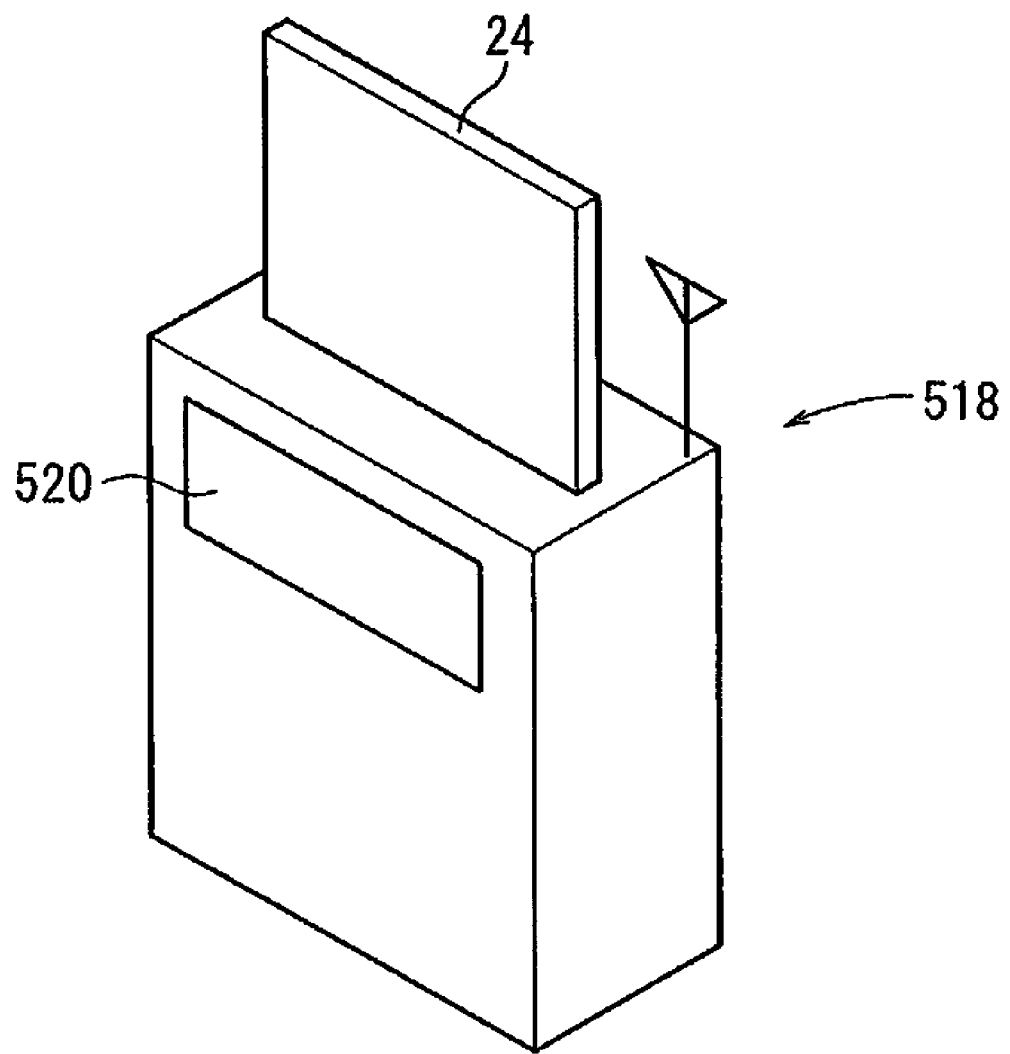
FIG. 11 is a perspective view showing a cradle which charges the radiation detecting cassette.

Preferably, a cradle 518 may be disposed in the medical examination room 12 or at a desired place in the hospital, into which the cassette 24 is inserted to charge the internal power supply 43, as shown in FIG. 11. In this case, in addition to charging the power supply 43, the cradle 518 may transmit and receive necessary information to and from external devices such as HIS 31, RIS 29, the console 28, etc. by way of wireless or wire communications of the cradle 518. The information may include radiation image information which is recorded on the cassette 24 inserted into the cradle 518.

Also, the cradle 518 may be provided with a display section 520. The display section 520 may display necessary information including a charging state of the inserted cassette 24 and radiation image information acquired from the cassette 24.

Further, a plurality of cradles 518 may be connected to a network. In this case, information about charging states of cassettes 24 inserted in respective cradles 518 can be collected through the network, and the cassette 24 in a usable state can be located.

The invention claimed is:

1. A radiation detecting cassette comprising:
a radiation conversion panel which detects a radiation having passed through a subject and converts the detected radiation into radiation image data;
a wireless communication unit which transmits said radiation image data by way of wireless communications;
a wired communication unit which transmits the radiation image data by way of wired communications;
a control unit which controls said radiation conversion panel, said wireless communication unit and said wired communication unit;
a power supply which energizes said radiation conversion panel, said wireless communication unit and said wired communication unit;
a remaining power level detecting unit which detects a remaining power level of said power supply; and
a display,
wherein said control unit controls said wireless communication unit to stop transmitting said radiation image data by way of wireless communications and controls said display to display a message requesting connection between said wired communication unit and an external device by a cable, as a result of the detected remaining power level of said power supply being detected as smaller than a predetermined threshold, and
in case that said wired communication unit is connected to the external device by said cable, said control unit controls said wired communication unit to transmit said radiation image data by way of wired communications to the external device.

* * * * *